United States Patent [19]
Brand

[11] Patent Number: 5,930,000
[45] Date of Patent: Jul. 27, 1999

[54] LINE-LOCKED DIODE LASER FOR GAS SPECTROSCOPY

[75] Inventor: Joel A. Brand, Colorado Springs, Colo.

[73] Assignee: Monitor Labs, Inc., Englewood, Colo.

[21] Appl. No.: 09/023,012

[22] Filed: Feb. 11, 1998

[51] Int. Cl.$^6$ .................................................. G01N 21/00
[52] U.S. Cl. .......................... 356/437; 250/343; 356/409
[58] Field of Search ..................................... 356/409, 326, 356/324, 325, 437, 343, 300; 250/345, 343; 372/32

[56] References Cited

U.S. PATENT DOCUMENTS

| | | |
|---|---|---|
| 3,995,960 | 12/1976 | Fletcher et al. . |
| 4,234,258 | 11/1980 | Margolis et al. . |
| 4,509,130 | 4/1985 | Menzies et al. . |
| 4,535,241 | 8/1985 | Eberhardt . |
| 4,934,816 | 6/1990 | Silver et al. . |
| 5,015,099 | 5/1991 | Nagai et al. . |
| 5,026,991 | 6/1991 | Goldstein et al. . |
| 5,173,749 | 12/1992 | Tell et al. . |
| 5,252,060 | 10/1993 | McKinnon et al. . |
| 5,267,019 | 11/1993 | Whittaker et al. . |
| 5,317,156 | 5/1994 | Cooper et al. . |
| 5,331,409 | 7/1994 | Thurtell et al. . |
| 5,436,459 | 7/1995 | Koch et al. . |
| 5,459,574 | 10/1995 | Lee et al. . |
| 5,550,636 | 8/1996 | Hagans et al. . |

*Primary Examiner*—K P Hantis
*Attorney, Agent, or Firm*—Fields and Johnson, P.C.

[57] ABSTRACT

An apparatus and method are disclosed for measuring the concentration of gases that are unstable or difficult contain in a sample cell. A frequency modulated laser is tuned to the frequency of a first spectral feature of a gas of interest and a laser beam is projected through a reference cell containing, at a selected pressure, a selected second gas that has a second spectral feature near the first spectral feature of the gas of interest. The laser is line-locked to an outer zero crossing of a third harmonic of the detected laser beam coincident with the first spectral feature. The concentration of the gas of interest is calculated from a second harmonic of a portion of the laser beam projected through a transmission medium containing the gas.

21 Claims, 3 Drawing Sheets

LINE-LOCKED DIODE LASER FOR GAS SPECTROSCOPY

TECHNICAL FIELD

The present invention relates to gas spectroscopy and more particularly to a method and apparatus of line-locking a tunable diode laser for gas concentration measurement.

BACKGROUND ART

Gas absorption spectroscopy measures the concentration of a species of gas of interest in a gas sample by passing an electromagnetic signal through the sample and detecting the absorption at the wavelength of a spectral absorption feature of the species of interest. A spectral feature is an absorption line representing a frequency of electromagnetic radiation corresponding to a vibrational, rotational or electronic transition of a molecule of the gas. Tunable diode lasers are ideal for absorption spectroscopy since these lasers can be tuned to the center of a spectral feature and these lasers provide a narrow signal relative to the width of the spectral feature. Temperature adjustment provides coarse tuning and DC current adjustment provides fine tuning of the laser diode to a frequency near the center of the spectral feature.

In Frequency Modulation Spectroscopy (FMS) a small AC signal is superimposed on top of the DC current of the diode laser to modulate the frequency of the laser beam across the center of the spectral feature. The modulated laser beam is passed through a sample of gas to a photodetector that measures the intensity of the laser beam. Absorption is greatest at the center of the spectral feature and absorption reduces as the frequency of the laser sweeps away from the center. As the laser frequency is modulated across the center, a periodic signal is produced by the photodetector. This resulting signal is expanded in a Fourier Cosine Series, the coefficients of expansion being denoted as harmonics. The fundamental or first harmonic is analyzed to monitor the transmitted laser power. The even harmonics exhibit maxima at the linecenter of the spectral feature and the second harmonic is analyzed to compute the concentration of the gas of interest.

The initial tuning of the laser results in the laser projecting a beam with a frequency near the center of the spectral feature. After initial tuning, the frequency of the laser beam can drift due to temperature and current variation. Line-locking the laser means preventing frequency drift and maintaining the modulated frequency of the laser beam centered at the desired frequency. The odd harmonics exhibit zero crossings at the center of the spectral feature. In conventional FMS systems the center zero crossing of the third harmonic is monitored to provide closed-loop control of the laser to line-lock the laser to the center of the spectral feature. FMS provides fast, accurate measurement and can detect trace gases in a sample.

If the gas of interest is difficult to contain in a reference cell, such as a highly corrosive gas or a short lived gas, the diode laser cannot be line-locked by monitoring the third harmonic of the gas of interest in a reference cell. In U.S. Pat. No. 5,459,574 to Lee et al., a tunable diode laser is first line-locked to the frequency of a spectral feature of a first gas in a reference cell and then the frequency is displaced a predetermined amount to the frequency of a spectral feature of a second gas to measure concentration of the second gas. The laser is free running and not line-locked during the measurement portion of the cycle. The laser is not line-locked to the second frequency and can only be maintained at this second frequency for a limited period of time.

DISCLOSURE OF THE INVENTION

The present invention provides an apparatus and a method of closed-loop control of a tunable diode laser at any frequency of interest. The method allows the measurement using gas spectroscopy of gases that cannot be easily captured. In the present invention, a laser is modulated across an absorption feature in a reference gas and the resulting signal is expanded in a Fourier Cosine Series, the coefficients of expansion being denoted harmonics. The odd harmonics exhibit a zero crossing at the line center of the absorption feature and exhibit outer zero crossings. The even harmonics also exhibit outer zero crossings. The location of the outer zero crossings depends on the modulation amplitude and also depends linearly on the pressure of the gas. The pressure of the gas is adjusted so that an outer zero crossing of a third or higher order harmonic of the reference gas coincides with the frequency of interest and the tunable diode laser is line-locked to the outer zero crossing. This method is not limited to the field of spectroscopy and can be used to line-lock a diode laser to any frequency of interest. The method could be used to provide standards for wavelength division multiplexing in optical communications system.

BRIEF DESCRIPTION OF THE DRAWINGS

Details of this invention are described in connection with the accompanying drawings that bear similar reference numerals in which.

DETAILED DESCRIPTION OF THE INVENTION

Figure 1:
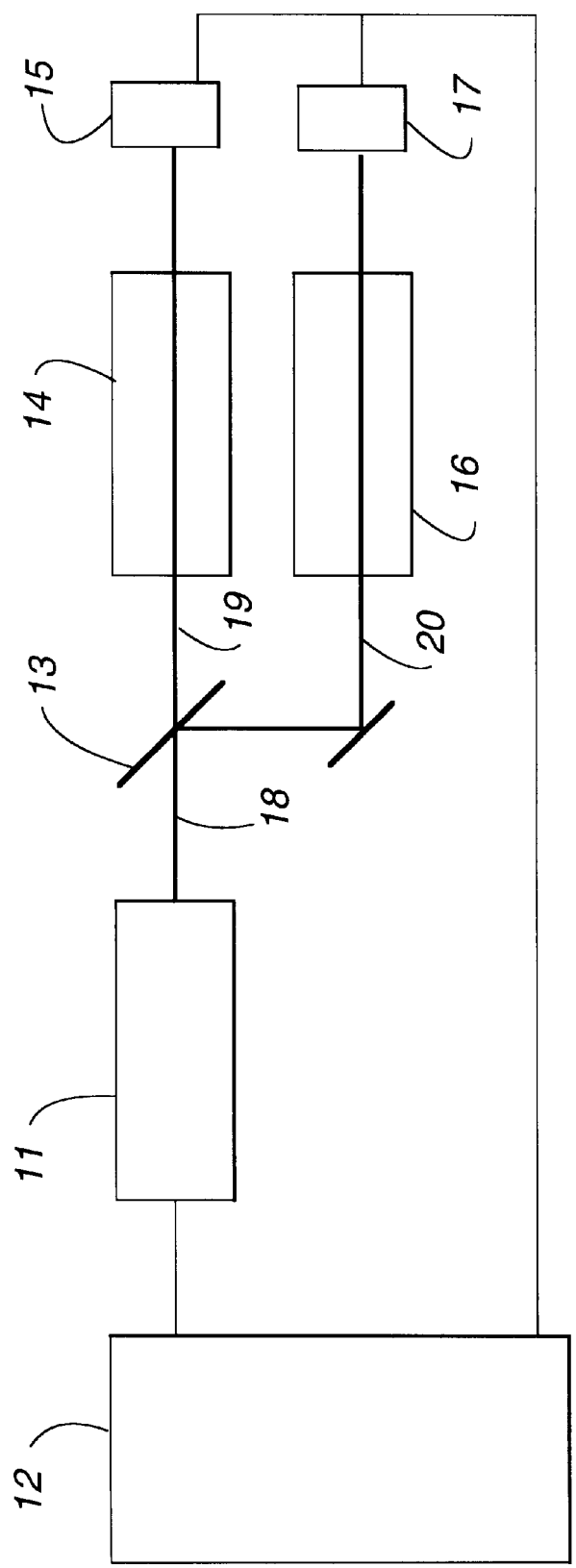
FIG. 1 is a schematic block diagram showing an apparatus embodying features of the present invention.

Referring now to FIG. 1, the apparatus for measuring concentration of a sample gas shown, generally stated, includes a laser 11, controller 12, a beamsplitter 13, a reference cell 14, a reference detector 15, transmission medium 16, and a sample detector 17.

Controller 12 includes electronic circuitry that controls the frequency of laser beam 18 projected by laser 11 and modulates the frequency of laser beam 18. A frequency at which a gas absorbs electromagnetic energy is known as a spectral feature or absorption feature. Spectral features have finite width and the center of a spectral feature is the linecenter. Laser 11 is tuned to project laser beam 18 at the frequency of the linecenter of a spectral feature of the sample gas selected for measurement. Coarse wavelength adjustment of laser 11 is accomplished by temperature tuning and fine adjustment is accomplished by adjusting the DC operating current of the laser 11. Laser beam 18 is wavelength modulated by superimposing a small AC current on top of the DC current.

Beamsplitter 13 splits laser beam 18 into a first beam portion 19 and a second beam portion 20. First beam portion 19 of laser beam 18 is projected from beamsplitter 13 through reference cell 14 to reference detector 15. Reference cell 14 contains a selected reference gas, different from the sample gas, at a selected pressure. Reference detector 15 measures the intensity of first beam portion 19 and provides an electrical signal proportional to the intensity to controller 12.

Second beam portion 20 of laser beam 18 is projected from beamsplitter 13 through transmission medium 16 to sample detector 17. Transmission medium 16 contains the gas sample to be monitored. Transmission medium 16 can be an open path through air, a closed sample cell or a multipass optical cell. Sample detector 17 measures the intensity of second beam portion 20 and provides an electrical signal proportional to the intensity to controller 12.

Controller 12 has electronic circuitry that expands the signal from reference detector 15 into the harmonics. Controller 12 monitors the third harmonic to maintain the frequency of laser beam 18 at the desired frequency to line-lock the laser 11. In the present invention, controller 12 uses an outer zero crossing of the third harmonic of the reference gas to line-lock laser 11 instead of the center zero crossing of the sample gas that has been used in prior known devices. Controller 12 also has electronic circuitry that expands the signal from sample detector 17 into the harmonics and uses the second harmonic to calculate the concentration of the sample gas in transmission medium 16.

Figure 2:
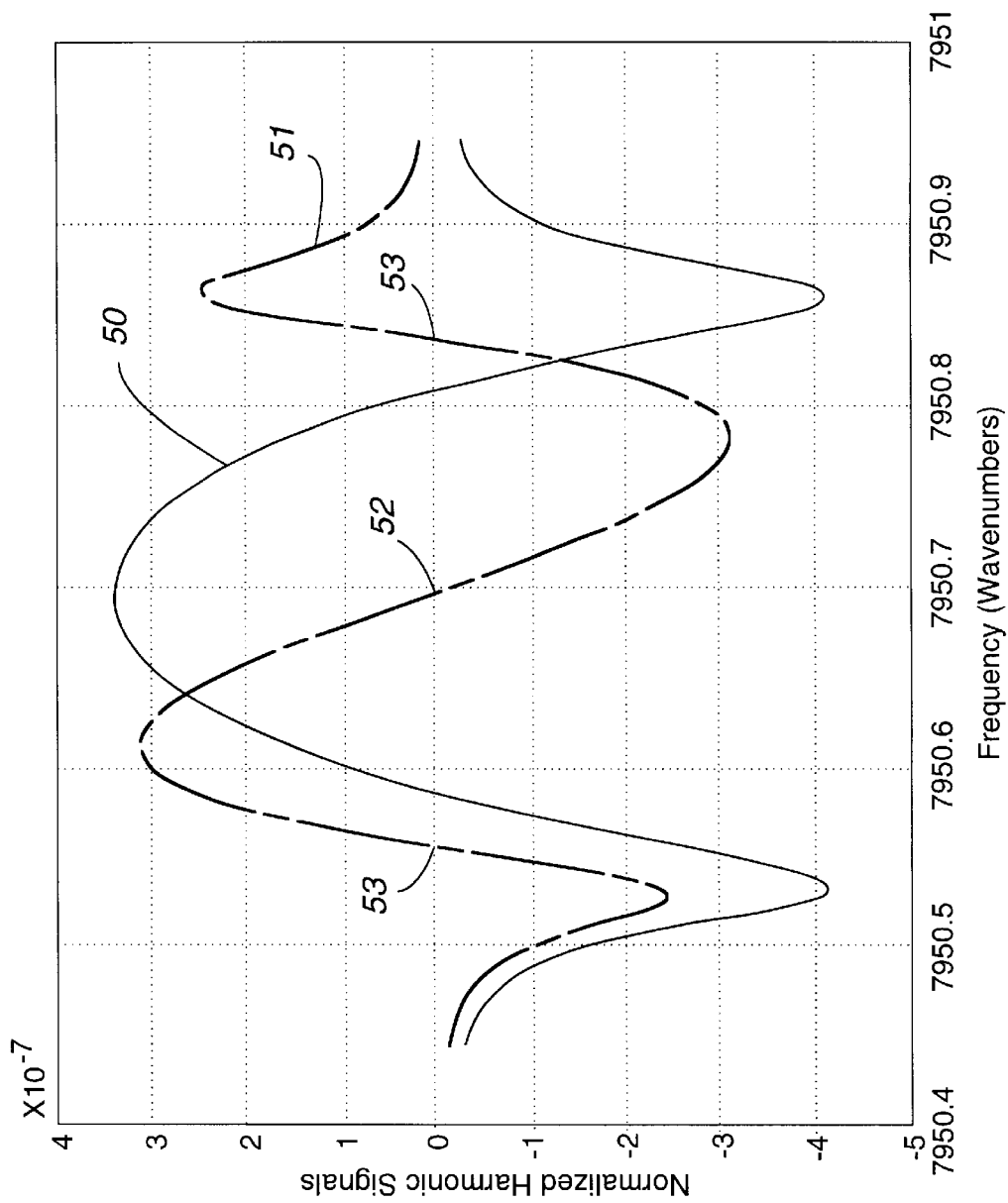
FIG. 2 is a graph showing the second and third harmonic components of a single gas.

Referring now to FIG. 2 the second harmonic 50 and third harmonic 51 of the 7950.69460 $cm^{-1}$ line in hydrogen fluoride (BY) are shown. Note that the third harmonic has a center zero crossing 52 at linecenter and also has two outside zero crossings 53. The location of the center zero crossing 52 is always at the linecenter. If the HF could be contained in a reference cell 14, a laser could be line-locked to the center zero crossing 52 of third harmonic 51 when measuring the concentration of HF in the transmission medium 16. HF, however, etches glass and is not easily contained or stable in a glass reference cell.

In the present invention the reference gas is selected such that the reference gas has a spectral feature separated from but near the spectral feature that will be used to measure concentration of the sample gas. The reference gas selected should also be stable and inert, and should be a gas that is expected to have low concentration in transmission medium 16 to avoid interference problems. The location of the outer zero crossings of a third harmonic depends on the modulation amplitude and the pressure. Correct adjustment of the modulation amplitude and the pressure of reference cell 14 provides an outer zero crossing coincident with the spectral feature that will be used to measure concentration of the sample gas.

Figure 3:
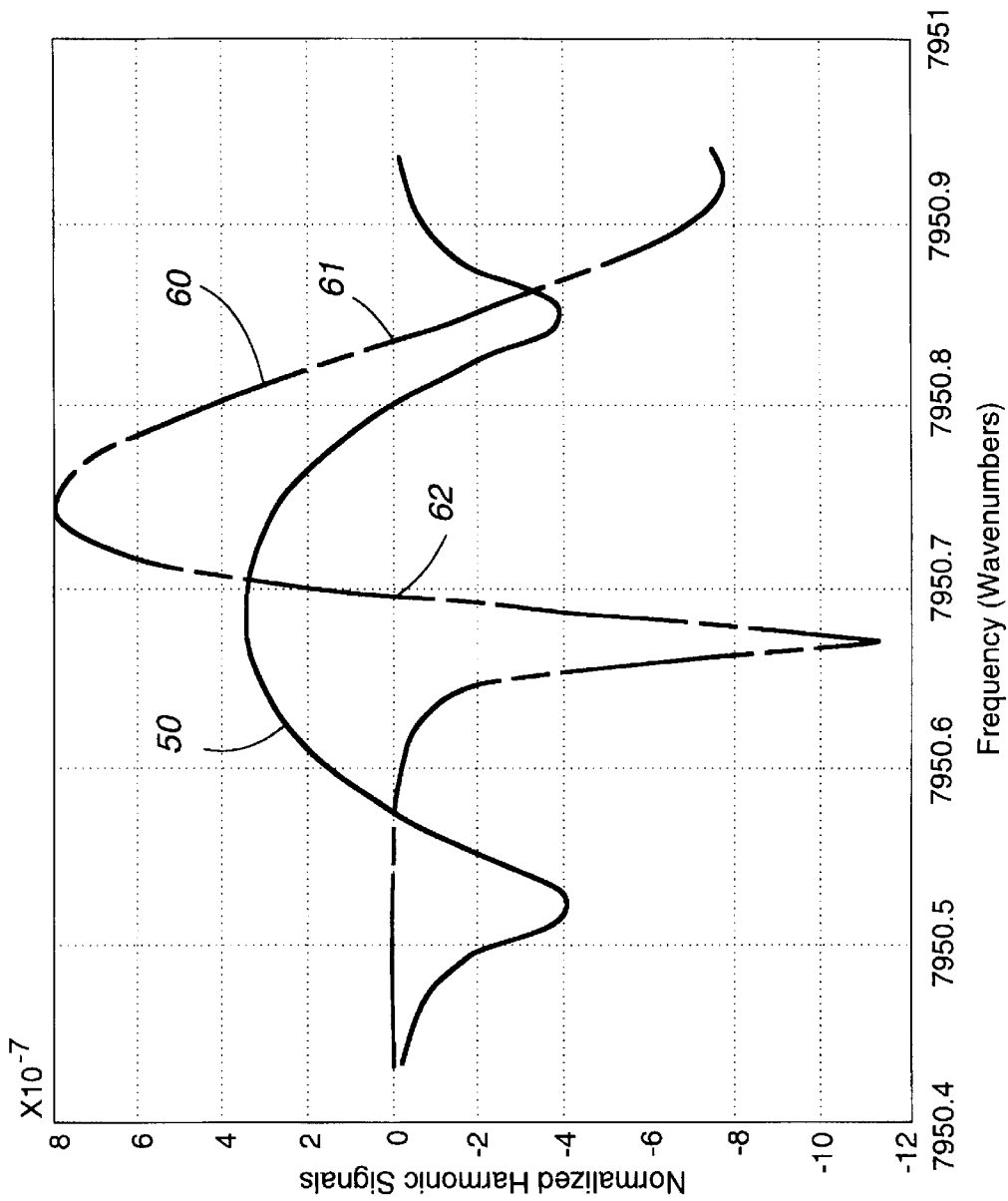
FIG. 3 is a graph showing the second harmonic component of a selected first gas and the third harmonic components of a selected second gas.

FIG. 3 shows the HF second harmonic 50 and a third harmonic 60 for the 7950.84359 $cm^{-1}$ line of carbon dioxide ($CO_2$) at 100 Torr with modulation amplitude of 0.17 $cm^{-1}$. The left outer zero crossing 62 for third harmonic 60 is coincident with the HF 7950.69460 $cm^{-1}$ line. For measuring the concentration of HF in transmission medium 16, reference cell 14 would be filled with $CO_2$ at 100 Torr and the laser would be line-locked to the left outer zero crossing 62 of the third harmonic 60.

Harmonics of order higher than three exhibit outer zero crossings that can also be used to line-lock a laser. The higher order harmonics will exhibit zero crossings further from the center of the spectral feature. However, the magnitudes of the harmonics decrease and bandwidth requirements for the processing electronics increase as the order of the harmonics increases.

This apparatus and method is not limited to the field of spectroscopy and can be used to line-lock a diode laser to any frequency of interest. Referring again to FIG. 1, an apparatus to line-lock a laser includes laser 11, controller 12, reference cell 14, and reference detector 15. The method could be used to provide standards for wavelength division multiplexing in optical communications system.

Although the present invention has been described with a certain degree of particularity, it is understood that the present disclosure has been made by way of example and that changes in details of structure may be made without departing from the spirit thereof.

What is claimed is:

1. Apparatus for measuring concentration of a sample gas in a transmission medium comprising:

a laser projecting a laser beam, said laser beam being tuned to a frequency corresponding to a spectral feature of said sample gas and, said laser beam being frequency modulated at a selected modulation amplitude;

a beamsplitter that splits said laser beam into a first beam portion and a beam second portion;

a reference cell containing a selected reference gas at a selected pressure;

a first detector, said first beam portion being projected from said beamsplitter through said reference cell to said first detector, said first detector measuring an intensity of said first beam portion and producing an electrical first signal proportional to said intensity of said first beam portion;

a second detector, said second beam portion being projected from said beamsplitter through the transmission medium to said second detector, said second detector measuring an intensity of said second beam portion and producing an electrical second signal proportional to said intensity of said second beam portion;

a controller that receives said first signal from said first detector and said second signal from second detector, said controller separating said first signal into harmonics including a line-locked harmonic and separating said second signal into harmonics including a second harmonic;

said reference gas being selected such that said reference gas has a spectral feature near said spectral feature of said sample gas;

said reference gas, said selected pressure of said reference gas, and said modulation amplitude being selected such that an outer zero crossing of said line-locked harmonic of said first signal is coincident with said frequency of said laser beam; and said controller controlling said laser and monitoring said line-locked harmonic to line-lock said laser beam at said outer zero crossing, said controller monitoring said second harmonic of said second signal to calculate concentration of said sample gas.

2. The apparatus as set forth in claim 1 wherein:

said line-locked harmonic is a third harmonic.

3. The apparatus as set forth in claim 2 wherein:

said sample gas is hydrogen fluoride;

said spectral feature of said sample gas is on the order of 7950.69460 $cm^{-1}$;

said reference gas is carbon dioxide;

said spectral feature of said reference gas is on the order of 7950.84359 $cm^{-1}$;

said pressure is on the order of 100 Torr; and said modulation amplitude is on the order of 0.17 $cm^{-1}$.

4. The apparatus as set forth in claim 1 wherein:

said line-locked harmonic is of a harmonic order greater than two.

5. Apparatus for line-locking a tunable laser to a selected frequency comprising:

a laser controller that initially tunes said laser to project a laser beam at the selected frequency and modulates said laser beam at a selected modulation amplitude;

a reference cell containing a reference gas at a selected pressure, said reference gas having a spectral feature spaced from but near said selected frequency; and a detector, said laser beam being projected through said reference cell to said detector, said detector measuring intensity of said laser beam, producing an electrical signal proportional to said intensity, and inputting said signal to said laser controller; and said laser controller separating said signal into harmonics and monitoring an outer zero crossing of a selected harmonic of said harmonics to line-lock the laser to the selected frequency.

6. The apparatus as set forth in claim 5 wherein:

said selected harmonic is a third harmonic.

7. The apparatus as set forth in claim 6 wherein:

said selected frequency is on the order of 7950.69460 $cm^{-1}$;

said reference gas is carbon dioxide;

said spectral feature of said reference gas is on the order of 7950.84359 $cm^{-1}$;

said pressure is on the order of 100 Torr; and said modulation amplitude is on the order of 0.17 $cm^{-1}$.

8. The apparatus as set forth in claim 5 wherein:

said selected harmonic is of a harmonic order greater than two.

9. A method of measuring concentration of a sample gas comprising the steps of:

line-locking a laser to project a laser beam at a frequency corresponding to an outer zero crossing of a selected harmonic of a spectral feature of a reference gas at a selected pressure, said frequency being coincident with a spectral feature of the sample gas; and measuring absorption of a beam portion of said laser beam at said frequency by said sample gas to calculate said concentration of the sample gas.

10. The method set forth in claim 9 wherein the step of line-locking includes the steps of:

modulating said laser beam at a selected modulation amplitude;

projecting said laser beam through said reference gas;

detecting said laser beam and producing an electrical signal proportional to an intensity of said laser beam;

separating said signal into orders of harmonics; and adjusting said laser beam in response to said selected harmonic to maintain said laser beam centered at said frequency.

11. The method as set forth in claim 10 wherein:

said selected harmonic is a third harmonic.

12. The method as set forth in claim 10 wherein:

said selected harmonic is of a harmonic order greater than two.

13. The method as set forth in claim 11 wherein:

said sample gas is hydrogen fluoride;

said spectral feature of said sample gas is on the order of 950.69460 $cm^{-1}$;

said reference gas is carbon dioxide;

said spectral feature of said reference gas is on the order of 7950.84359 $cm^{-1}$;

said pressure is on the order of 100 Torr; and said modulation amplitude is on the order of 0.17 $cm^{-1}$.

14. A method of measuring concentration of a sample gas in a gas sample comprising the steps of:

providing a reference cell containing a reference gas at a selected pressure, said reference gas and said selected pressure being chosen such that a harmonic of a spectral feature of said reference gas at said selected pressure has an outer zero crossing at a frequency corresponding to a spectral feature of said sample gas;

projecting a modulated laser beam from a laser tuned to project said laser beam centered at said frequency through said reference cell to a detector;

producing an electrical signal proportional to an intensity of said laser beam with said detector;

separating said signal into orders of harmonics;

maintaining said laser beam centered at said outer zero crossing; and measuring absorption of said laser beam by said sample gas to calculate said concentration of said sample gas.

15. The method as set forth in claim 14 wherein said harmonic is third harmonic.

16. The method as set forth in claim 14 wherein said harmonic is of a harmonic order greater than two.

17. The method as set forth in claim 15 wherein:

said sample gas is hydrogen fluoride;

said spectral feature of said sample gas is on the order of 7950.69460 $cm^{-1}$;

said reference gas is carbon dioxide;

said spectral feature of said reference gas is on the order of 7950.84359 $cm^{-1}$;

said pressure is on the order of 100 Torr; and said modulation amplitude is 0.17 $cm^{-1}$.

18. A method of line-locking a laser to a frequency comprising the steps of:

projecting a laser beam from the laser and modulated at a selected modulation amplitude from said laser through a reference cell containing a reference gas at a predetermined pressure, said reference gas having a spectral feature spaced from but near the frequency;

detecting said laser beam with a photodetector;

converting said laser beam to an electric signal;

expanding said signal into harmonics;

monitoring a selected harmonic of said harmonics, said selected harmonic having an outer zero crossing at the frequency; and adjusting said laser beam in response to said selected harmonic to maintain said laser beam centered at the frequency.

19. The method as set forth in claim 18 wherein:

said selected harmonic is a third harmonic.

20. The method as set forth in claim 18 wherein:

said selected harmonic is of a harmonic order greater than two.

21. The method as set forth in claim 20 wherein:

the frequency is on the order of 7950.69460 $cm^{-1}$;

said reference gas is carbon dioxide;

said spectral feature of said reference gas is on the order of 7950.84359 $cm^{-1}$;

said pressure is on the order of 100 Torr; and said modulation amplitude is on the order of 0.17 $cm^{-1}$.

* * * * *